United States Patent
Hole et al.

(10) Patent No.: US 9,909,970 B2
(45) Date of Patent: Mar. 6, 2018

(54) CALIBRATION OF INSTRUMENTS

(71) Applicant: Malvern Instruments Limited, Worcestershire (GB)

(72) Inventors: John Patrick Hole, Worcestershire (GB); Jonathan Benjamin Kendall Smith, Worcestershire (GB); Ian John Wilson, Worcestershire (GB); Andrew Paul Malloy, Worcestershire (GB)

(73) Assignee: Malvern Instruments Limited, Worcestershire (GB)

( * ) Notice: Subject to any disclaimer, the term of this patent is extended or adjusted under 35 U.S.C. 154(b) by 0 days.

(21) Appl. No.: 15/037,888

(22) PCT Filed: Nov. 7, 2014

(86) PCT No.: PCT/GB2014/053314
§ 371 (c)(1),
(2) Date: May 19, 2016

(87) PCT Pub. No.: WO2015/075424
PCT Pub. Date: May 28, 2015

(65) Prior Publication Data
US 2016/0290911 A1  Oct. 6, 2016

(30) Foreign Application Priority Data
Nov. 20, 2013  (GB) .................. 1320475.5

(51) Int. Cl.
*G01J 3/28* (2006.01)
*G01N 15/06* (2006.01)
(Continued)

(52) U.S. Cl.
CPC ............ *G01N 15/06* (2013.01); *G01N 1/28* (2013.01); *G01N 15/0227* (2013.01);
(Continued)

(58) Field of Classification Search
CPC ...... G01N 15/05; G01N 1/28; G01N 15/0227; G01N 33/483; G01N 2001/2893;
(Continued)

(56) References Cited

U.S. PATENT DOCUMENTS

2006/0256338 A1* 11/2006 Gratton .............. G01N 15/1463
356/417
2010/0315639 A1  12/2010 Muraki

FOREIGN PATENT DOCUMENTS

| EP | 2584343 A1 | 4/2013 |
| WO | 2011/059485 A2 | 5/2011 |
| WO | 2012/004320 A1 | 1/2012 |

OTHER PUBLICATIONS

"Measurement of filtration efficiency of Nuclepore filters challenged with polystyrene latex nanoparticles: experiment and modeling", Journal of Nanoparticle Research; vol. 13, No. 10, Aug. 11, 2011, pp. 5414-5424, by Tsz et al.*
(Continued)

*Primary Examiner* — Jamil Ahmed
(74) *Attorney, Agent, or Firm* — Morgan, Lewis & Bockius LLP (57) ABSTRACT

Disclosed is a method of calibrating apparatus for optically characterizing samples of particles of small size. Also disclosed is a method of estimating the concentration of particles in a population of small size particles.

17 Claims, 4 Drawing Sheets

(51) Int. Cl.
*G01N 15/02* (2006.01)
*G01N 1/28* (2006.01)
*G01N 33/483* (2006.01)
*G01N 15/00* (2006.01)
*B82Y 35/00* (2011.01)

(52) U.S. Cl.
CPC ............ *G01N 33/483* (2013.01); *B82Y 35/00* (2013.01); *G01N 2001/2893* (2013.01); *G01N 2015/0038* (2013.01); *G01N 2015/0065* (2013.01); *G01N 2015/0294* (2013.01); *G01N 2015/0693* (2013.01); *Y10S 977/901* (2013.01)

(58) Field of Classification Search
CPC ........... G01N 2015/0038; G01N 15/06; G01N 15/02; G01N 21/64; B82Y 35/00
See application file for complete search history.

(56) References Cited

OTHER PUBLICATIONS

Ling et al., "Measurement of filtration efficiency of Nuclepore filters challenged with polystyrene latex nanoparticles: experiments and modeling," Journal of Nanoparticle Research, 13: 5415-5424 (2011).

Du et al., "Measuring number-concentrations of nanoparticles and viruses in liquids on-line," Journal of Chemical Technology and Biotechnology, 85: 1223-1228 (2010).

Gallego-Urrea et al., "Applications of particle-tracking analysis to the determination of size distributions and aoncentrations of nanoparticles in environmental, biological and food samples," Trends in Analytical Chemistry, 30: 173-483 (2011).

International Search Report issued in corresponding International Patent Application No. PCT/GB2014/053314 dated Jan. 26, 2015.

* cited by examiner

CALIBRATION OF INSTRUMENTS

FIELD OF THE INVENTION

The present invention relates to a method of calibrating an instrument, especially an instrument for optical detection or analysis of particles, to an instrument calibrated by the method, and to a method of estimating the concentration of particles (in terms of number of particles per unit volume) in a sample.

BACKGROUND OF THE INVENTION

The present invention is especially pertinent to apparatus and methods for performing nanoparticle tracking analysis ("NTA").

Nanoparticle tracking analysis is a relatively recently developed method for the direct and real-time visualisation and analysis of nanoparticles in liquids (see e.g. WO 03/093801). Based on a laser-illuminated microscopical technique, Brownian motion of nanoparticles is analysed in real-time by, for example, a charge-couple device (CCD) camera or the like, each individual particle being simultaneously but separately visualised and tracked by a dedicated particle tracking image-analysis programme. The ability of NTA to measure simultaneously particle size and particle scattering brightness allows heterogeneous particle mixtures to be resolved and, importantly, particle concentration to be estimated directly, the particle size distribution profile obtained by NTA being a direct number/frequency distribution.

NTA has become a term of art, recognised by those skilled in the relevant field. There are over 900 scientific papers and presentations referring to data collected using NTA. Further the term is used by, for example, ASTM International (formerly the American Society for Testing and Materials), the Environmental Protection Agency (EPA), the Food and Drug Administration (FDA) and the NIH.

The range of particle sizes that can be analysed by NTA depends on the particle type. The lower size limit is defined by the particle size and particle refractive index, given that sufficient light must be scattered by each particle for it to be detected and tracked as described above. For particles with very high refractive indices, such as colloidal gold, accurate determination of size can be achieved down to particles with a maximum dimension of about 10 nm. For lower refractive index particles, such as those of biological origin, the smallest detectable size might be in the range 25-50 nm Accordingly, NTA is limited by its ability to detect particles below a certain size.

With NTA, the presence and analysis of particles, each of which scatters sufficient light to be detected individually, can still be carried out even in the presence of 'background' material comprising, for instance, a population of very small particles (such as protein molecules, sub-10 nm inorganic material, polymer solutions, nano-emulsions, etc.) each of which is too small to detect individually but which is present in sufficiently high concentration to collectively form a background haze of scattered light. This background cannot be analysed by NTA, but particles visible as discrete light scattering entities embedded within this background may be analysed by NTA. Of course, the intensity of this background will determine the limit of sensitivity of NTA in terms of minimum detectable size. Further, NTA is able to identify, track and analyse suitably sized particles even when they are present in heterogeneous samples containing low numbers of larger particles.

NTA is further capable of detecting and analysing inherently fluorescent or fluorescently-labelled nanoparticles in the presence of a non-fluorescent background through use of appropriate fluorescence exciting optical sources and suitable fluorescence filters. NTA is further capable of measuring more than one fluorescence wavelength within a sample using multiple filters or a colour camera.

The sizing of individual nanoparticles by NTA is based on the analysis of Brownian motion exhibited by micron and sub-micron particles suspended in a liquid when illuminated by a suitable light source (e.g. laser) such that the light scattered by the particles is detected by a microscopical arrangement which causes some of the light scattered by the particles to be imaged by a video camera (typically CCD, electron multiplying CCD [EMCCD], scientific complementary metal oxide semiconductor [sCMOS] etc.).

The average distance moved by any given particle at known time intervals (e.g. the reciprocal of the frame rate of the camera, typically 30 frames per second) is related through the Stokes Einstein equation in which the diffusion coefficient can be extrapolated to particle hydrodynamic diameter, if the temperature and viscosity of the surrounding liquid are known.

The region of laser beam interrogated by the camera is a function of the size (in the x and y dimensions) of the image captured by the microscopical optical train onto which is fitted a suitable camera. For usual applications, a ×20 long working distance microscope objective is used. Because Brownian motion is effectively independent of particle mass, NTA (like the related technique of Dynamic Light Scattering) is considered an absolute technique, not requiring calibration. Because it interrogates particles individually within a suspension (though simultaneously), it is possible to generate high resolution particle size distribution profiles.

The field of view of the camera is typically about 100×80 microns and the depth of beam has previously been assumed to be approximately 10 μm.

However, the spatial dimensions (including "depth") of the laser beam in which any given particle is visible to the camera (the 'effective scattering volume' or observation volume) is, especially given the frequently non-uniform intensity profile of the laser sources used, dependent on a variety of factors. These include the inherent sensitivity of the camera (adjustable by varying gain and shutter settings), the power and wavelength of the laser beam and, most importantly, is a strong function of the size and refractive index of the scattering particles.

The illuminating laser beams are not usually top-hat in profile (i.e. of uniform intensity throughout both the x and y dimensions) but are complex, ranging from a smooth Gaussian (or similar) profile to very complex profiles in which unpredictable spatial variations in cross-sectional intensity arise from the optical perturbations on launching the beam into the scattering cell through a glass wall at low (close to critical) angle.

Accordingly, while is it possible to dynamically determine with some confidence the particle size distribution of the particles successfully tracked by NTA, accurate estimation of the number of particles of any given size or size class present in the path of the laser beam is more problematical.

Put simply, smaller and/or lower refractive index particles are often only visible (to the camera) in the regions of the beam in which the incident intensity is highest (e.g. the centre of a Gaussian beam or brighter parts of, for example, a striated beam) and are not visible in lower intensity regions. In contrast, larger (or higher refractive index) particles can be seen at greater distances from the high intensity beam centre (or between high intensity striations) because they scatter more light. Thus for two such particle types the volume in which they are visible (the "effective observation volume") will be different and consequently, even though they may be actually present in the same number concentration, NTA will detect different numbers of particles in the same system.

WO 2012/004320 discloses a method by which the effective observation volume can be determined by measuring the average track length of a particle moving under Brownian motion in a beam. With knowledge of the temperature and viscosity in which a particle of known size (or, more accurately, known diffusion coefficient) is moving, the length of time such a particle will be, on average, present and therefore scattering detectable amounts of light and thus trackable, will depend (all other things being equal) on the volume of the interrogation region. Larger effective 'observation volumes' result in longer track-lengths for any given sized particle.

In other words, the larger the beam (or more effective the particle is as a scatterer), the longer will be a particle's visible lifetime in the beam. If the size of a particle is known (e.g. because using a calibration particle) and the temperature and viscosity of the solvent is known, it is possible to calculate the volume of the beam from determining the track-length distribution of a monodisperse population of particles of a known size. Using this 'absolute' method by which the scattering volume can be spatially calculated, it is possible to determine the number of particles seen in a volume calculated, allowing generation of an absolute value for number concentration of the sample. However the limitations of this technique are that it assumes a continuous and uniform observation volume, and requires an accurate measurement of track length which could be significantly affected at high particle concentrations, with a high image noise or with a flowing sample.

Another technique for calibrating NTA apparatus is disclosed by Gardiner et al ("Extracellular vesicle sizing and enumeration by nanoparticle tracking analysis" Journal of Extracellular Vesicles 2013, 2 1-11). This involves the use of a calibration sample of a particular nanoparticle population of known concentration, having similar characteristics (in terms of particle size and refractive index) to a particle population to be analysed.

However, the method is of limited practical usefulness, requiring a calibrant particle with appropriate properties (which may not always be available) and, in any event, the apparatus requires re-calibration each time if it is to be used to analyse a population of particles with different properties.

The present invention aims to reduce or overcome one or more of the problems associated with the prior art.

SUMMARY OF THE INVENTION

In a first aspect, the invention provides a method of calibrating apparatus for optically characterising samples of particles of small size (i.e. less than 1000 nm diameter); comprising the steps of:
(a) introducing into the apparatus a sample of a calibration population of particles which is (i) substantially monodisperse (e.g. diameter S.D. is less than 10% mean diameter) and (ii) homogeneous and (iii) has a known concentration of particles in terms of number per unit volume;
(b) analysing the sample, under appropriate conditions to determine, for a particular combination of apparatus conditions or settings, the number of particles detected and the average brightness individually of detected and measured particles;
(c) adjusting the apparatus to a new particular combination of apparatus conditions or settings and analysing the same sample, or another sample of the same calibration population as in step (a), and repeating the analysis of step (b) to determine the number of particles detected and the average brightness of detected particles under the new combination of apparatus conditions or settings;
(d) optionally repeating step (c) at one or more further new particular combinations of apparatus conditions or settings; and
(e) deriving from the analyses a calibration plot or look-up table of brightness of particle against number of particles detected, which is used to calibrate the apparatus against subsequent analysis of populations of particles of unknown concentration, to determine an estimate of the concentration thereof.

For present purposes, a substantially monodisperse population of particles is considered as one in which the diameter S.D. is less than 10% of the mean particle diameter. The person skilled in the art will also appreciate that the particles in question need not be perfectly spherical, but will preferably be at least substantially spherical. The concentration of particles (in terms of number per unit volume) in the calibration population is preferably known absolutely, or may be known to lie within a prescribed range (e.g. +/−20%, preferably +/−10%, more preferably +/−5%).

The method may involve determination of a total number of particles detected or, more preferably, determination of the number of particles detected per unit time. In practice, this is usually done per image frame.

In a second aspect, the invention provides a method of estimating the concentration of particles in a population of small size particles, the method comprising the steps of:
(i) calibrating suitable apparatus using a method in accordance with the first aspect of the invention defined above, or using apparatus so calibrated;
(ii) analysing a sample of the population, and determining the average number of particles detected; and the average brightness of the particles;
(iii) comparing the result from (ii) with that expected from the calibration plot or look-up table to arrive at an estimate of the actual particle concentration in the sample.

It will be appreciated that features of the invention which are preferred or desirable etc. in relation to the first aspect of the invention will generally apply equally to the second aspect of the invention.

The present invention is especially useful in relation to the calibration of apparatus employed to perform NTA, and to estimating the concentration of particles in a population using apparatus performing NTA, although in principle other particulate imaging techniques could benefit from the invention.

The invention is typically useful for analysing or characterising samples in which the particles have a mean diameter or dimension generally in the range 10-1000 nm, more typically 20-750 nm, although as described previously, the minimum size of particle detectable by NTA is dependent at least in part on the refractive index of the particle, with more highly refractive particles being easier to detect.

The particles may be anything of appropriate size and refractive index and may be biological or non-biological in nature. The sample may be any engineered or naturally-occurring sample comprising nanoparticles. Particular examples of nanoparticulate samples which may be analysed by NTA and which might therefore be of interest in the methods of the present invention include, but are not limited to, the following: viruses (including bacteriophages), vaccine formulations comprising attenuated or inactivated viruses or virus-like particles and the like; protein aggregates; exosomes; membrane aggregates and liposomes; inks and pigments; quantum dots; and chemical mechanical polishing/planarization ("CMP") slurries.

The method of the invention is preferably performed using a monodisperse population of particles as hereinabove defined.

In addition, the method of the invention may be used to estimate the concentration of particles in a sample which contains two or more different monodisperse populations of particles of sufficiently different size to be resolvable by means of NTA.

Step (a) of the method of the invention requires the use of a sample of a standard calibration sample of particles the concentration of which is known at least approximately (e.g. to within an order of magnitude). Suitable samples are available commercially from Thermo Scientific (e.g. 3000 Series Nanosphere Size Standards) and BBI solutions (e.g. gold nanoparticles) and such particles may comprise for example, particulate gold nanospheres or polystyrene beads. The commercially available samples may require dilution with a diluent to provide a sample having a particulate concentration in a range suitable for analysis. The diluent should obviously be free of particulates which might interfere with the analysis. Water, a buffer or other aqueous solution as appropriate may be used as a diluent.

Step (b) of the method requires an analysis of the calibrant sample using the apparatus to be calibrated. The apparatus will typically be apparatus adapted and configured to perform NTA. The apparatus will therefore generally comprise a light source (usually a laser), an optical stage or specimen chamber or the like, and an optical detector, such as a CCD or the like, typically together with computer processing means to perform the necessary imaging and particle tracking analysis, and associated software.

The various components of the apparatus will have adjustable settings, which can be adjusted to allow the apparatus to be used to analyse samples having different properties (principally such as particle size, particle refractive index and particle concentration). For example, (especially in apparatus adapted and configured to perform NTA), it will generally be possible to adjust various settings, either manually or by altering values in the associated software, which settings determine the effective observation volume within which particles may be detected and tracked. These include, in particular (i) those relating to the sensitivity of the detector device; and (ii) those relating to the brightness detection threshold. Where the optical detector is a CCD or similar, the variable settings include, for example, the camera gain or the shutter speed. The brightness detection threshold is an adjustable threshold, set by the user, which determines the minimum brightness of an observable particle to be selected for analysis and tracking. Sources of light within the effective observation volume which are detected but which do not match or exceed the brightness detection threshold are disregarded.

Accordingly, using NTA apparatus as one exemplary embodiment, step (b) of the method may be performed using one specific, particular combination of the aforementioned settings (and optionally other settings as well), to analyse the calibration sample to determine the number of particles and the average brightness thereof.

In step (c), the process of step (b) is repeated, using either the same sample as in step (a), or a replicate sample of the same calibration population. If the same sample is used, it may be necessary to ensure that the particles are kept homogenised within the effective observation volume (e.g. by occasional agitation). In step (c) however, one of the aforementioned (e.g. camera) settings which determine the effective observation volume is altered relative to its setting in step (b), so as to form a new specific combination of settings (and therefore create a different effective observation volume). The number of particles and the average brightness thereof is again determined.

In step (d) the above process is optionally (but preferably) repeated using a further particular combination of settings which determine the effective observation volume. Again, the same sample may be used, or a replicate sample of the same calibration population. This step is preferably iterated many times, each time using a different particular combination of settings, such that a data set can be built up with numbers of particles detected and average brightness thereof over a wide range of different effective observation volumes, so that the apparatus can be calibrated over a wide range of settings, thereby allowing the calibrated device to be used to analyse many different samples of interest which may have widely differing properties in terms of size, refractive index, etc.

The data set acquired by the analyses may then be used to produce a plot of brightness of particles against number of particles detected, or a look-up table. Using the known (or assumed) concentration of the particle population used, the observation volume can be inferred from number of particles detected, resulting in a plot of brightness of particles against observation volume. This plot or table, or its informational equivalent, is then conveniently stored in a digital memory device operably attached or associated with the apparatus, so that the apparatus can refer to the data and make appropriate adjustment to arrive at a corrected estimate of particle concentration when, in future, used to analyse an actual test sample of interest having an unknown observation volume, and hence unknown particle concentration.

In a third aspect the invention provides apparatus suitable for calculating the concentration (in terms of number per unit volume) of small-sized particles, the apparatus being calibrated by the method of the first aspect of the invention, and having a digital memory device which stores, in digital form, a plot or look-up table or its informational equivalent, produced by the calibration method of the first aspect.

Preferably the apparatus is adapted and configured to perform NTA. The apparatus will thus preferably comprise one or more, or all, of the sort of components used in commercially-available NTA apparatus, such as a CCD or EMCCD and/or microscope; a sample chamber; sample-handling fluidics (tubing, pumps etc); sample illumination device (e.g. a laser); processing means programmed with nanoparticle-tracking image analysis software etc; and a digital memory device.

It is further preferred that the apparatus comprises, or is operably associated with, computer processing means which is programmed to produce a corrected estimate of particle concentration for a sample analysed by the apparatus, the corrected estimate being determined by applying a calibration factor from the data stored in the digital memory device.

The invention will be further described by way of illustrative example, and with reference to the accompanying drawings, in which.

EXAMPLES

Example 1

Calibration using 100 nm polystyrene standards

Figure 1:
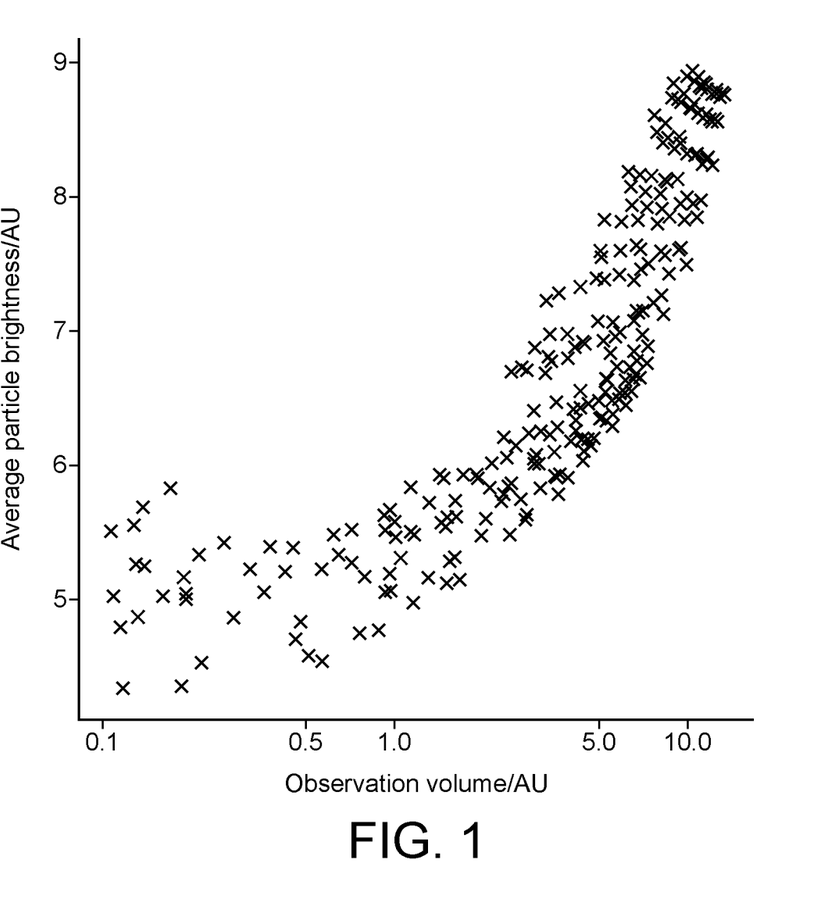
FIG. 1 is a graph of average particle brightness (arbitrary units) against observation volume (arbitrary units), showing data obtained with a monodisperse population of 100 nm diameter polystyrene beads, used in one example of a calibration method in accordance with the invention.

Firstly, the standard is diluted to an appropriate concentration, e.g. $10^8$ particles/ml, and injected into appropriate measuring apparatus (such as the NanoSight NS500 system, NanoSight, Amesbury, UK). Several measurements are made at the range of different camera settings (shutter and gain) and detection settings (detection threshold). Data is filtered so that points with limited statistics or high noise are removed. Using the remaining data, observation volume is calculated using the known concentration and the number of particles counted, and this is plotted against average brightness for a number of detection thresholds as seen in FIG. 1.

Linear regression is performed on the data using average brightness as the main explanatory variable. To deal with other settings (such as detection threshold), either separate models can be made and the variable can be integrated into the regression model as a variate or factor (in this case, detection threshold is an additional explanatory variable).

Figure 2:
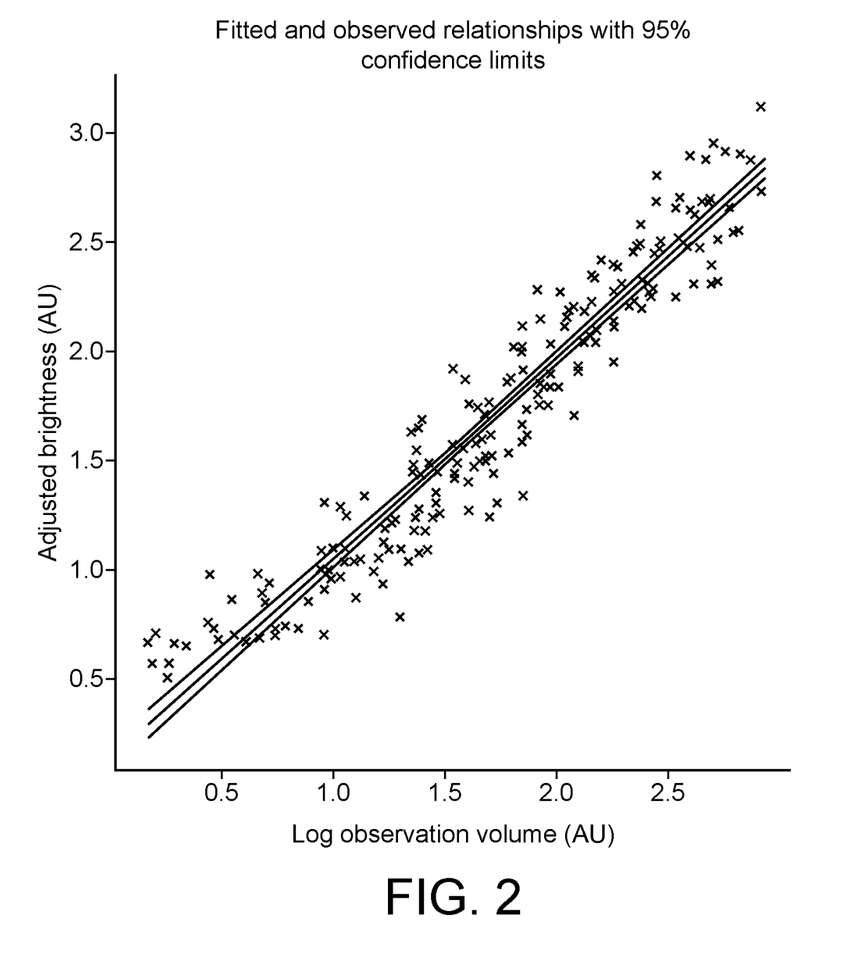
FIG. 2 is a graph of adjusted log n observation values against brightness showing a linear relationship.

The fit to the data is shown in FIG. 2 plotting the observation volume on AU scale against brightness (mlni_5).

This linear model can then be used to predict the observation volume for a measurement of any brightness (modified via camera settings, size, refractive index etc. . . . ) and concentration.

Figure 3A:
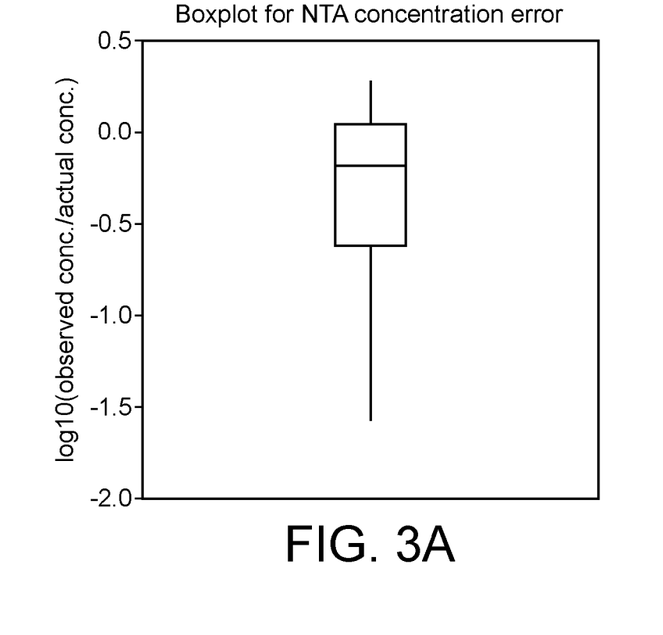
FIG. 3A and FIG. 3B show box plots of $\log_{10}$ (observed concentration/actual concentration) for a sample analysed by NTA before (FIG. 3A) and after (FIG. 3B) calibration according to the invention.
Figure 3B:
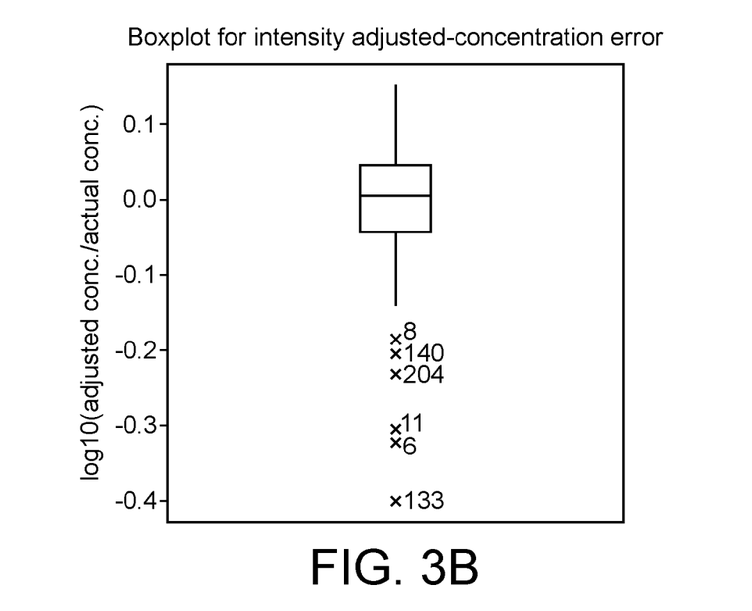

Applying the model to the range of 100 nm particles used for the calibration significantly reduces variation. The boxplot in FIG. 3A and FIG. 3B variation before calibration (FIG. 3A), and right, after calibration (FIG. 3B: note log scale)

The Figure demonstrates that prior to applying the process, there was an observed interquartile variation (due primarily to camera settings and detection threshold) of ~0.7 logs=(i.e. a factor of about 500%) variation, whereas after applying the process, the interquartile variation was ~30%.

Figure 4:
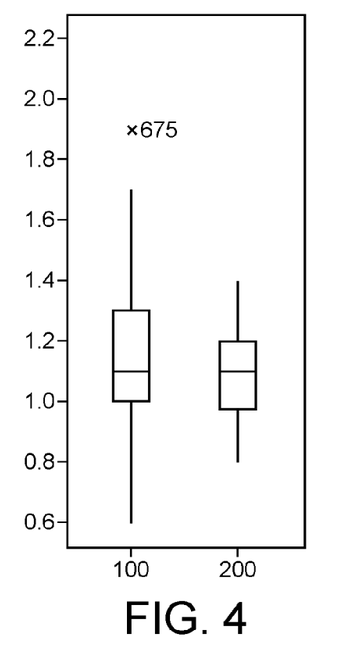
FIG. 4 shows box plots of observed concentration/actual concentration for two different populations of particles (100 or 200 nm in diameter) following performance of a calibration method in accordance with the invention.

Further, applying the model to additional sets of 100 nm particles and 200 nm particles (captured with a similar range of settings) gave comparable results (see FIG. 4; note, not on log scale):

This example illustrates the principles of the invention as applied to methods and apparatus for performing nanoparticle tracking analysis ("NTA").

The present inventors have appreciated that, in contrast to the approach described in WO2012/004320, one can obtain an idea of the effective scattering volume (from which an estimate of number concentration can be obtained) by measuring the intensities of light scattered by particles and calibrating against a population of known number concentration.

Thus, for a monodisperse (size calibrant) population of particles of known number concentration (numbers of particles per unit volume), the number of such particles seen in any given optical configuration and setup e.g. laser wavelength and power, camera sensitivity and settings, etc.) can be adjusted to the real number concentration through calibration. If one or more of the parameters responsible for the brightness of the particles seen is adjusted (e.g. the laser power is increased or the camera sensitivity increased [gain, shutter length]) then the number of such particles seen will increase. So for a calibration sample of particles, it is possible to generate a 'primary' calibration graph of average number of particles seen and counted for any given detection efficiency. Changing the detection sensitivity of the system (e.g. by increasing camera gain) thus changing the 'particle brightness' will result in a corresponding change in number of particles seen. Similarly, if the calibrant sample is diluted, a change in the number seen (compared to what was expected from the calibration graph) reflects a real change in the actual number present.

For a different sample (e.g. different size and/or refractive index), if the sample is monodisperse and homogeneous, the brightness of the particles seen (even following changing of the sensitivity [e.g. camera gain] of the system) can be compared to the calibration graph and the actual number of particles per unit volume (its concentration) estimated. The primary calibration graph can thus be seen to be applicable to any other monodisperse and homogeneous sample type given that the average brightness of a particle type reports on the effective scattering volume of that particle type and therefore its number concentration can be confidently estimated.

Measurements obtained using fluorescent particles (either inherently fluorescent, or fluorescently-labelled), instead of measurements made using light scattered by the particles, may alternatively be used in the calibration technique.

To reiterate, following calibration of the scattering volume to particle number using a monodisperse and homogeneous sample of known number concentration, other monodisperse and homogeneous samples (even of different scattering properties arising from different size and/or Ri) can be counted and the number concentration estimated as long as the brightness is adjusted (through, for instance, camera gain or laser power) to fall in the range of the primary number calibration graph. Difference in average numbers of particles seen from that expected from the primary calibration graph are therefore indicative of real differences in the actual number concentration of the new sample.

For a bimodal sample comprising of two different particle types with adequately different scattering properties (through size and/or refractive index) the two populations will, if an adequate number of each of the particle populations are detected, resolve themselves into two data sets each of which can, using the primary calibration graph, be separately counted and the concentrations of each adjusted according to their position on the calibration graph.

For mixtures containing multiple populations of particle types, the resolution with which they can be discriminated becomes increasingly problematical with increasing polydispersity and/or variation in any other measurable parameters such as brightness, size, polarization, fluorescence, shape, motive forces (such as electrical, magnetic, gravitational etc.) or any other measurance capable of differentiating the sample. However, dividing the data into (either separate or overlapping) bins or groups of increasing resolution will assist in increasing accuracy of counting in such complex samples, providing sufficient numbers of particles are present in each bin or group observed.

Of course, unlike other optical techniques which rely on the measurement of particle intensity for sizing and counting, NTA is capable of measuring the dynamic Brownian motion of particles (individually) from which can be estimated particle size. Because this analysis is operating in the time domain, it is independent of the particle's intensity. This allows an additional orthogonal measureand to be exploited in the brightness/concentration relationship described above.

Thus, for different particle populations each of different size and/or Ri but whose light scattering properties are similar and would therefore not be capable of being distinguished from each other in on an intensity basis alone, it is possible (given each particle is being simultaneously detected, Brownian motion sized and brightness measured) to discriminate and count (using the primary calibration graph) such particle populations by plotting their brightness against size against calibrated number concentration.

Similarly, other measureands afforded by NTA could be exploited in this way. For example, fluorescently labelled particles, behaviour in applied motive fields (e.g. electrical, magnetic, gravitational, etc.), particle shape, polarization etc. could each or variously be employed to advantage.

Example 2

Figure 5:
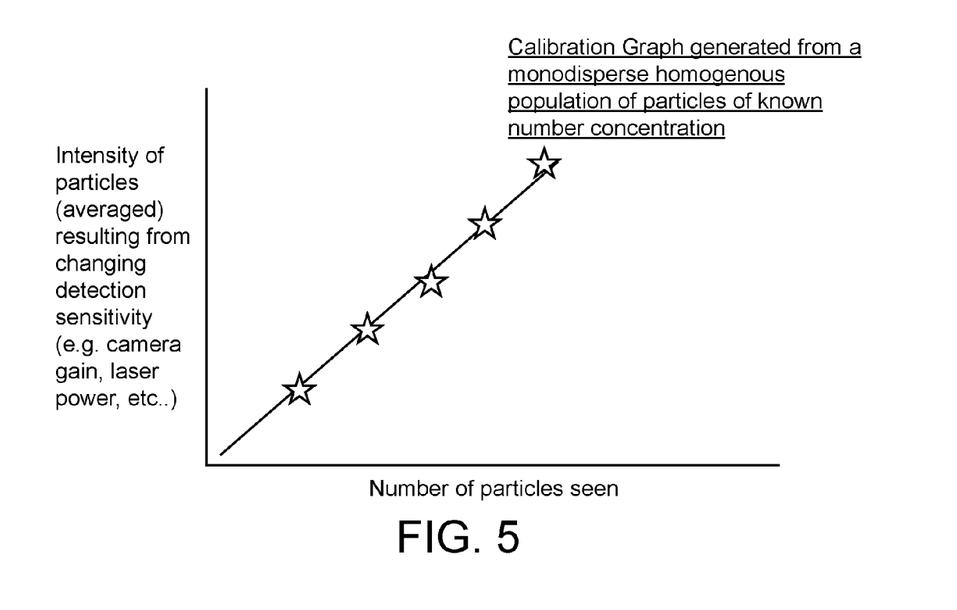
FIG. 5 is a generalized, representative graph of apparent particle brightness against number of particles seen per unit time (e.g. per image frame).

An example of the calibration method of the invention, as applied to NTA apparatus is described below.
Method
Steps required to number calibrate a system from which numbers of a different sample type can be determined:
Number Calibration
 1. For a NanoSight system of arbitrary beam profile and power, add a suitably diluted sample (to anywhere between $10^7$-$10^9$ particles/ml) of monodisperse and homogeneous calibration quality particles (e.g. of a size in the range 10-1000 nm or more preferably 50-300 nm whose number concentration is accurately known.
 2. Carry out analyses using a range of shutter and gain settings, to adequately cover the range of intensities which NTA analysis can effectively measure.
 3. Perform above analysis until adequately by robust statistics are obtained through analysing a sufficient number of analysed particle tracks over a sufficient time. As a minimum this would normally be >200 tracks and greater than 30 seconds and more preferably >1000 analysed particle tracks and greater than 150 seconds.
 4. Measure average brightness displayed by particles seen at selected camera settings and count average number of particles detected per unit time (e.g. per frame).
 5. Use resultant data to generate a calibration graph of particle brightness differences (through increasing gain) resulting in a corresponding increase in particles seen per unit time, as illustrated schematically in FIG. 5.
 6. Assuming the absolute number concentration of the calibration sample to be known, scattering volume can be inferred from the average number of particles seen, hence generating a calibration curve of brightness and scattering volume.
 7. Using resultant calibration graph to find a [linear or otherwise] relationship between the average apparent particle brightness and scattering volume.

Having performed the calibration procedure above, it is possible then to use the information so obtained to determine an estimate of particle concentration for any particulate sample which is analysable using NTA.

The estimation of particle concentration is performed thus:
 8. Add sample of suitably diluted but otherwise unknown sample to instrument (without changing alignments or magnifications) and adjust settings (e.g. camera gain/shutter or laser power) until average brightness of particles seen lies within range of intensities exhibited by particles used in calibration graph above.
 9. Analyse sample, logging average brightness (and size) of particles detected.
 10. Using average brightness data obtained, use the relationship found in Step 7 to infer the scattering volume in which the particles are visible.
 11. Once scattering volume is known the number of particles counted can now be related to particle concentration in the sample.

Measurement of Multimodal Samples of Unknown Concentration, Composition and Size
 12. For samples which contain two or more discrete populations of different sample types/size ranges carry out Steps 8 and 9 above.
 13. Identify the two or more discrete groupings arising from recognisably different brightness groups, calculate scattering volume and resultant concentration for each discrete group as per Steps 10 and 11.
 14. Apply different number adjustments for as many different sub-populations as can be identified.

Use of Additional Measureands Available from NTA to Extract Further Information from Complex Sample Types For samples containing a plurality of sub-populations which can be discriminated by adding further information about each particle (e.g. size as determined by Brownian motion, electrophoretic mobility under an applied electric field, fluorescence generated by specific labels (e.g. antibody mediated)) replot in three dimensions (brightness v. concentration v. size/fluoresce signal/mobility/etc.) and recover corrected number estimates from calibration graph).

The invention claimed is:
1. A method of calibrating apparatus for optically characterising samples of particles of small size comprising the steps of:
 (a) introducing into the apparatus a sample of a calibration population of particles which is (i) substantially monodisperse and (ii) homogeneous and (iii) has a known concentration of particles in terms of number per unit volume;
 (b) analysing the sample, under appropriate conditions to determine, for a particular combination of apparatus conditions or settings, the number of particles detected and the average brightness of individually detected and measured particles;
 (c) adjusting the apparatus to a new particular combination of apparatus conditions or settings and analysing the same sample, or another sample of the same calibration population as in step (a), and repeating the analysis of step (b) to determine the number of particles detected and the average brightness of detected particles under the new combination of apparatus conditions or settings; and

(d) deriving from the analyses a calibration plot or look-up table of brightness of particle against number of particles detected, which is used to calibrate the apparatus against subsequent analysis of populations of particles of unknown concentration, to determine an estimate of the concentration thereof.

2. The method according to claim 1, wherein step (c) comprises adjusting a camera setting and/or a brightness detection threshold.

3. The method according to claim 2, wherein the camera setting adjusted comprises camera gain, shutter speed or frame rate.

4. The method according to claim 1, wherein the calibration plot or look-up table derived in step (d), or its digital informational equivalent, is stored in a digital memory device operably attached or associated with the apparatus.

5. A method of estimating the concentration of particles in a population of small size particles, the method comprising the steps of:
(i) either calibrating suitable apparatus using the method in accordance with claim 1, or using apparatus already so calibrated;
(ii) analysing a sample of the population, and determining the average number of particles detected; and the average brightness of the particles; and
(iii) comparing the result from (ii) with that expected from the calibration plot or look-up table to arrive at an estimate of the actual particle concentration in the sample.

6. The method according to claim 5, wherein the sample of particles comprises one of the following: viruses (including bacteriophages), vaccine formulations comprising attenuated or inactivated viruses or virus-like particles and the like; protein aggregates; exosomes; membrane aggregates and liposomes; inks and pigments; quantum dots; and chemical mechanical polishing/planarization ("CMP") slurries.

7. The method according to claim 5, wherein the sample analysed in step (ii) is polydisperse and/or varies over a measured parameter.

8. The method according to claim 7, wherein measured data obtained from the sample in step (ii) are divided into two or more groups of differing resolution, the groups being either discrete or overlapping.

9. The method according to claim 5, wherein step (ii) comprises obtaining data regarding one or more parameters of the particles in addition to average number and average brightness.

10. The method according to claim 9, wherein the one or more additional measured parameters is/are selected from: polarizing characteristic; fluorescence; shape; and movement under application of a motive force.

11. The method according to claim 1, wherein the apparatus is adapted and configured to perform NTA.

12. The method according to claim 11, wherein the apparatus comprises one or more of the following components: a CCD, EMCCD and/or a microscope; a sample chamber; sample-handling fluidics; sample illumination device; processing means programmed with nanoparticle-tracking image analysis software; and a digital memory device.

13. An apparatus suitable for optically characterizing particles of small size, calibrated by the method of claim 1.

14. A nanoparticle tracking analysis (NTA) apparatus according to claim 13, in which the calibration information is stored in a digital memory device operably attached or associated with the apparatus.

15. The method according to claim 5, wherein the apparatus is adapted and configured to perform NTA.

16. The method according to claim 8, further comprising respectively estimating the concentration of particles for each of the two or more groups.

17. The method according to claim 1, further comprising, prior to step (d), repeating step (c) at one or more further new particular combinations of apparatus conditions or settings.

* * * * *